(12) United States Patent
Wright et al.

(10) Patent No.: US 8,477,903 B2
(45) Date of Patent: Jul. 2, 2013

(54) VALIDATING A COMPENSATOR FOR USE IN A RADIATION THERAPY MACHINE TO TREAT A CANCER PATIENT

(75) Inventors: John M. Wright, Dorset (GB); William Tomer, Ben Avon, PA (US); Michael J. Hudson, Great Missenden (GB)

(73) Assignee: Axellis Ventures Ltd, Leicestershire (GB)

( * ) Notice: Subject to any disclaimer, the term of this patent is extended or adjusted under 35 U.S.C. 154(b) by 307 days.

(21) Appl. No.: 13/077,456

(22) Filed: Mar. 31, 2011

(65) Prior Publication Data

US 2012/0250824 A1 Oct. 4, 2012

(51) Int. Cl.
*A61N 5/10* (2006.01)

(52) U.S. Cl.
USPC .............................. 378/65; 378/156; 378/159

(58) Field of Classification Search
USPC ............................................ 378/65, 156, 159
See application file for complete search history.

(56) References Cited

U.S. PATENT DOCUMENTS

| | | | |
|---|---|---|---|
| 4,623,288 A | 11/1986 | Brunelli et al. | |
| 5,432,704 A | 7/1995 | Vouzelaud et al. | |
| 5,596,504 A | 1/1997 | Tata et al. | |
| 5,625,663 A | 4/1997 | Swerdloff et al. | |
| 5,683,243 A | 11/1997 | Andreiko et al. | |
| 6,381,304 B1 | 4/2002 | Shoenfeld et al. | |
| 6,748,400 B2 | 6/2004 | Quick | |
| 6,980,871 B1 | 12/2005 | Sweat | |
| 7,162,008 B2 | 1/2007 | Earl et al. | |
| 2001/0044668 A1 | 11/2001 | Kimbrough et al. | |
| 2004/0186744 A1 | 9/2004 | Lux | |
| 2006/0015202 A1 | 1/2006 | Sweat | |
| 2007/0033786 A1 | 2/2007 | Bradley | |
| 2007/0226986 A1 | 10/2007 | Park et al. | |
| 2008/0027974 A1 | 1/2008 | Collins | |
| 2009/0287333 A1 | 11/2009 | Sweat | |
| 2009/0287334 A1 | 11/2009 | Sweat | |
| 2009/0316965 A1 | 12/2009 | Mailling et al. | |

FOREIGN PATENT DOCUMENTS

| | | |
|---|---|---|
| DE | 3340482 | 5/1985 |
| DE | 4102258 | 7/1992 |
| EP | 2108401 A1 | 10/2009 |
| WO | 99/58929 | 11/1999 |
| WO | 0045283 A1 | 8/2000 |
| WO | 01/82829 | 11/2001 |
| WO | 2010019504 A1 | 2/2010 |
| WO | 2011024085 A1 | 3/2011 |

OTHER PUBLICATIONS

International Search Report for PCT/GB2007/000303, mailed Jul. 29, 2008.

(Continued)

*Primary Examiner* — Thomas R Artman
(74) *Attorney, Agent, or Firm* — Brown Rudnick LLP

(57) ABSTRACT

A method of validating a compensator for use in a radiation therapy machine to treat a cancer patient involves determining a radiation treatment plan based on a compensator description file that includes data representative of an actual machined surface of the compensator. The plan includes operating parameters of the radiation therapy machine, and this plan is compared against actual radiation measurements taken during a non-patient test of the radiation therapy machine with the compensator mounted to the machine. If the comparison results in a match, the compensator is validated for use in the radiation therapy machine to treat the cancer patient.

10 Claims, 2 Drawing Sheets

OTHER PUBLICATIONS

Galvin et al: "Alternative Methods for Intensity-Modulated Radiation Therapy Inverse Planning and Dose Delivery," Seminars in Radiation Oncology, Saunders, Philadelphia, PA, vol. 16, No. 4, Oct. 1, 2006, pp. 218-223.

Chang S X et al: "Compensators: An alternative IMRT delivery technique," Journal of Applied Clinical Medical Physics, American College of Medical Physics, Melville, NY, vol. 5, No. 3, Jan. 1, 2004, pp. 15-36.

International Search Report and Written Opinion mailed Jun. 18, 2012 for PCT/IB2012/000793 (11 pages).

Anders Ahnesjö et al: "Review; The IMRT information process-mastering the degrees of freedom in external beam therapy", Physics in Medicine and Biology, Taylor and Francis Ltd. London, GB, vol. 51, No. 13, Jul. 7, 2006, pp. R381-R402.

International Search Report and Written Opinion mailed Jun. 12, 2012 for PCT/US2012/030706 (11 pages).

VALIDATING A COMPENSATOR FOR USE IN A RADIATION THERAPY MACHINE TO TREAT A CANCER PATIENT

TECHNICAL FIELD

The invention relates to improved validation of radiation-attenuating compensators (also known as radiation filters) for use in radiation therapy machines to treat cancer patients.

BACKGROUND INFORMATION

Intensity-modulated radiation therapy (IMRT) is a treatment method for accurately delivering a defined and uniform dose of radiation to a tumor site. This treatment method is designed to limit the amount of radiation to which peripheral non-cancerous tissues and structures are exposed. IMRT is used on cancer patients to deliver a uniform dose of radiation to a patient's cancerous tissue as defined by the clinician while avoiding, or at least minimizing, radiation exposure to the surrounding healthy or critical body structures of the patient. IMRT delivers radiation to the patient's cancerous tissue from various angles and at various intensity levels in order to achieve the prescribed dose profile for that patient. Patients with cancer can be treated with other types of radiation therapy such as proton radiation therapy or cobalt radiation therapy.

With IMRT and other types of radiation therapy, the intensity of the radiation beam can be varied or modulated by using a compensator. A compensator is also known as a radiation filter. The compensator is mounted directly in the path of a radiation beam generated by a radiation therapy machine, before the beam reaches the patient. Each compensator is made specifically for a particular patient and also for each angle (field) from which radiation is delivered. Existing practice utilizes compensators machined from a solid piece of material. The unique patient-specific three-dimensional geometry of each machined finished compensator provides the conformal radiation dose distributions required by that particular cancer patient to treat their tumor according to the prescribed dose. In general, a compensator created for one cancer patient cannot effectively be used for the treatment of another cancer patient. Individual compensators are used from each beam angle (field) during a course of IMRT treatment, requiring a change of compensator for each discrete field of radiation treatment. Compensators are typically provided in "sets" for a treatment plan for a specific patient.

Patient-specific compensators can be machined in-house at a hospital or other radiation treatment facility, or the compensators can be ordered from a $3^{rd}$ party supplier such as an outside machine shop. One outside machine shop from which compensators can be ordered is .decimal, Inc of Sanford, Fla. (www.dotdecimal.com). After manufacturing the ordered compensator, the outside machine shop physically delivers that set of compensators to the requesting treatment facility, typically by shipping it to the facility using a general carrier.

Before any compensator is mounted to a radiation therapy machine and used in the radiation treatment of an actual patient, the compensator must be validated in a quality assurance (QA) process. If the compensator does not pass the QA check, it will not be used in the radiation treatment of a cancer patient.

SUMMARY OF THE INVENTION

A treatment planning system (TPS) is conventionally used to validate compensators before they are used with a radiation therapy machine to actually deliver radiation treatment to a cancer patient. In accordance with the invention, the TPS does not use the existing "theoretical model" of the compensator to validate the corresponding real-world compensator, but instead the TPS uses a "new model" that more accurately represents the actual machined or formed surface of the compensator. The TPS calculates a radiation treatment plan for each particular cancer patient, including the necessary beam intensity and all other operating parameters of the radiation therapy machine needed to deliver to the patient with the selected radiation machine the necessary radiation treatment when the machine has the compensator mounted to it. In the invention, the appropriate beam intensity and other parameters for the machine (that together constitute the patient-specific radiation treatment plan) are calculated by the TPS using the new model representative of the actual surface of the compensator. An analysis tool can then compare that calculated radiation treatment plan to real-world measurements taken during the pre-treatment/non-patient test of the machine with the compensator mounted to it. If the comparison is close enough, such as a match of 80% or greater, or 85% or greater, then the real-world compensator is validated and considered to have passed a necessary quality assurance (QA) check. The validated compensator then can be used with the radiation therapy machine to deliver the radiation treatment plan to the actual cancer patient.

In one aspect, the invention relates to a method of validating a compensator for use in a radiation therapy machine to treat a cancer patient. The method comprises receiving a compensator description file including data representative of an actual machined surface of the compensator, and then determining a final radiation treatment plan based on that file. This plan includes operating parameters of the radiation therapy machine, and the plan is compared against actual radiation measurements taken during a non-patient test of the radiation therapy machine with the compensator mounted to the machine. If the comparison results in a match, the compensator is validated for use in the radiation therapy machine to treat the cancer patient. A correspondence of 80% or greater, or 85% or greater, between the plan and the test measurements can be the match criteria. The validated compensator can be used in intensity modulated radiation therapy (IMRT), proton radiation therapy, or cobalt radiation therapy, for example. And, the compensator could be formed of tungsten, brass, or aluminum, for example. The compensator could be, for example, a conventional compensator machined from a single solid piece of material, or the compensator could be one formed by compaction of particulates into a mold as disclosed in U.S. patent application Ser. No. 13/075,885 filed on Mar. 30, 2011. The entirety of U.S. patent application Ser. No. 13/075,885 is incorporated herein by reference.

Objects, advantages, and details of the invention herein disclosed will become apparent through reference to the following description, the accompanying drawings, and the claims. The various disclosed embodiments as well as each of the various features of those embodiments are not mutually exclusive and can exist in various combinations and permutations whether or not expressly pointed out in the following description or the accompanying drawings.

BRIEF DESCRIPTION OF THE DRAWINGS

In the drawings, like structures are referenced by the same or similar reference numbers throughout the various views. The illustrations in the drawings are not necessarily drawn to scale, the emphasis instead being placed generally on illustrating the principles of the invention and the disclosed embodiments.

DESCRIPTION

Figure 1:
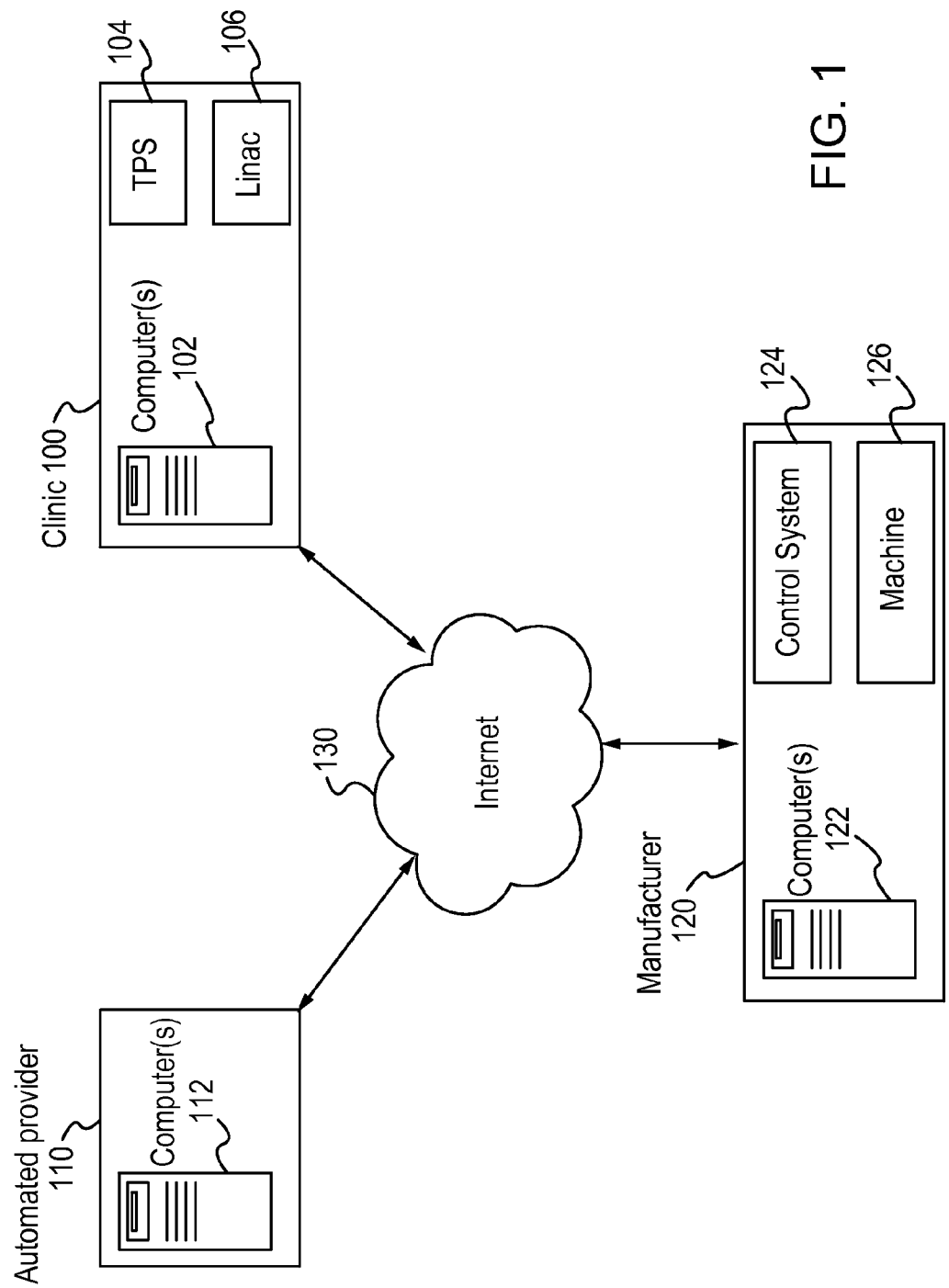
FIG. 1 is a block diagram showing the entities involved in defining, creating, and validating compensators for use with radiation therapy machines to treat cancer patients.

As shown in FIG. 1, the entities involved in defining, manufacturing, and creating patient-specific compensators for use with a radiation therapy machine at a radiation treatment clinic to treat a particular cancer patient include the clinic 100, an outside provider 110, and a manufacturer 120 such as a machine shop. The clinic 100 can be referred to as a radiation oncology treatment center, and it can be a hospital or any location where cancer patients are treated with radiation to address their cancerous tumors. Each clinic 100 typically will have at least one radiation therapy machine such as a linear accelerator 106 and also at least one supporting treatment planning system (TPS) 104. The linear accelerator 106 is also referred to as a "Linac". Linacs are available commercially from Varian Medical Systems, Inc. (of Palo Alto, Calif.) and also from Siemens Medical Solutions USA, Inc. (of Malvern, Pa.), for example. The TPS 104 is available commercially from Varian under the name "Eclipse" and also from other vendors which use other product names for their treatment planning systems. The clinic 100 typically also will have at least one computer 102 such as a general purpose desktop computer with the typical components including at least one processor, memory (such as RAM and/or ROM), one or more other storage mechanisms or devices (hard drive, for example), at least one display screen, one or more input devices such as a keyboard and/or a mouse, a web browser application such as "Internet Explorer" by Microsoft Corporation of Redmond, Wash., and in general the ability to store instructions in the memory and/or storage devices (more generally, computer-readable media) that are executed by the processor(s) to cause the processor, and thus the computer 102, to perform various functions such as web browser functions as well as other functions. A user of the computer 102 can access the World Wide Web via the Internet 130 by launching and using the computer's web browser. Someone at the clinic 100 also could use the TPS 104 to access the Web via the Internet 130 by launching and using a web browser that the TPS 104 might have access to. As is typical, the Internet 130 is represented in FIG. 1 as a "cloud" which is a metaphor for the Internet. The cloud 130 can be any type of computer or communications network but in the disclosed embodiment is the Internet. Someone at the clinic 100 can use the computer(s) 102 to communicate over the network 130 with one or more server computers 112 located at the outside provider 110. The computer(s) 112 can be one or more web servers and/or other types of computers such as application servers. With the computer(s) 112, the provider 110 can communicate via the network 130 with the clinic 100 and also with the manufacturer 120. (While the one or more servers 112 are shown located at the provider 110, it is noted that they do not have to be physically at the same geographic location of the provider 110, and instead one or more or all of the servers 112 could be located at some location remote from the provider 110. That is, some or all of the services and functions performed by the provider 110 could be outsourced or hosted on one or more servers 112 located remote from the business address of the provider 110.) One or more of the computer(s) 112 can execute a computer aided manufacturing (CAM) system, such as the commercially available piece of software called SurfCAM by Surfware, Inc. of Camarillo, Calif. 93012 (www.surfware.com) or another CAM software application available from another software vendor. The manufacturer 120 includes at least one computer 122 and equipment to create one or more physical compensators and/or one or more physical molds into which solid particulates (such as crystalline tungsten powder) can be compacted to form compensators. Any compensator-creating and mold-creating equipment located at the manufacturer 120 can include at least one machine control system 124 and at least one controllable machine 126 such as a CNC machine. Once one or more physical patient-specific compensators are created at the manufacturer 120, they can be shipped from the manufacturer 120 to the clinic 100 where they can be used, after validation, with the Linac 106 at the clinic 100 to treat the cancer patient for whom the compensators were made. If the manufacturer 120 has created patient-specific molds as opposed to finished compensators, the molds can be shipped to the clinic 100 and compacted with particulates at the clinic 100 to form finished compensators (as disclosed in the incorporated-by-reference U.S. patent application Ser. No. 13/075,885 filed on Mar. 30, 2011), and these types of mold-based compensators then can be used, after validation, with the Linac 106 at the clinic 100 to treat the cancer patient.

The process of defining and validating finished compensators according to the invention will be described with reference to FIGS. 1 and 2, but, first, it is noted that the radiation treatment regime for a cancer patient typically is determined by the clinical oncology staff at the clinic 100. This staff establishes the appropriate radiation dose to treat the patient's tumor. This established radiation dose is divided into a number of discrete deliveries, or beams, around the tumor in order to avoid over-dosing critical non-cancerous structures of the patient. The sum total of the beams being the total radiation delivery for the patient's treatment per day; the full course of treatment might take as many as 45 days to complete, for example. Using the TPS 104 configured with the specific radiation characteristics of the target treatment Linac 106, the clinical team imports computed tomography or CT images (sometimes also referred to as CT scans or computerized axial tomography or CAT images or scans) taken of the patient's tumor and surrounding structures, adds geometric profiles (boundaries) determining the areas to treat (and the areas to avoid), and enters the radiation dose required into the TPS 104. The TPS 104 then calculates the dose patterns for each beam. Typically, each of the dose patterns can be considered a grid of regularly shaped cells with each cell containing a value between 1 and 0, where 1 represents the maximum dose and 0 represents no radiation dose at all. The non-zero areas of a dose pattern are together referred to as the modulated zone. The Linac's 106 radiation beam needs to be modulated to create the necessary dose patterns to treat the cancer patient, and this is why compensators are created and used. Each compensator is designed and created to attenuate or modulate the radiation beam to provide the necessary amount of radiation to each of the cells in the grid. There are actually two ways to modulate the radiation beam of the Linac 106. One way is by using a Multi Leaf Collimator (MLC), and this involves a set of "fingers" that are automatically and programmatically driven into and out of the radiation beam's path to vary the amount of radiation. Another way is by placing in the beam's path a contoured block, and such a block is referred to as a compensator. It typically is, at least initially, more expensive to use an MLC to achieve the necessary modulated zone, because a Linac 106 with an MLC is more expensive than a Linac 106 that uses compensators. To provide the patient with that day's radiation treatment, each individual compensator of a set of patient-specific compensators is placed at the appropriate time in a frame of the Linac 106 called the accessory tray or accessory mount. When in place, the head of the Linac 106 is rotated to the appropriate beam position and the amount of radiation determined by the TPS 104 is delivered. The compensator is then replaced for the next in the beam sequence, and the process is repeated until all beams have been delivered to provide the patient with his or her radiation treatment for that day.

Prior to treating the patient with any radiation (whether the Linac 106 uses an MLC or compensators), the staff at the clinic 100 is required to check and verify that each beam delivers the radiation as planned by the TPS 104. To do this, a sensitive medium of either film or an electronic dose measurement device is placed on a treatment couch of the Linac 106, and then each beam is delivered and measured with the film or device. When compensators are used, the compensators are mounted to and used with the Linac 106 just as they would be during the actual treatment regime for the patient. The measured radiation delivery is then compared to the delivery calculated by the TPS 104, and only if they match is the treatment considered viable and the compensators validated for use. The match could be determined by, for example, meeting or exceeding a comparison threshold such as greater than 80% or greater than 85%.

Figure 2:
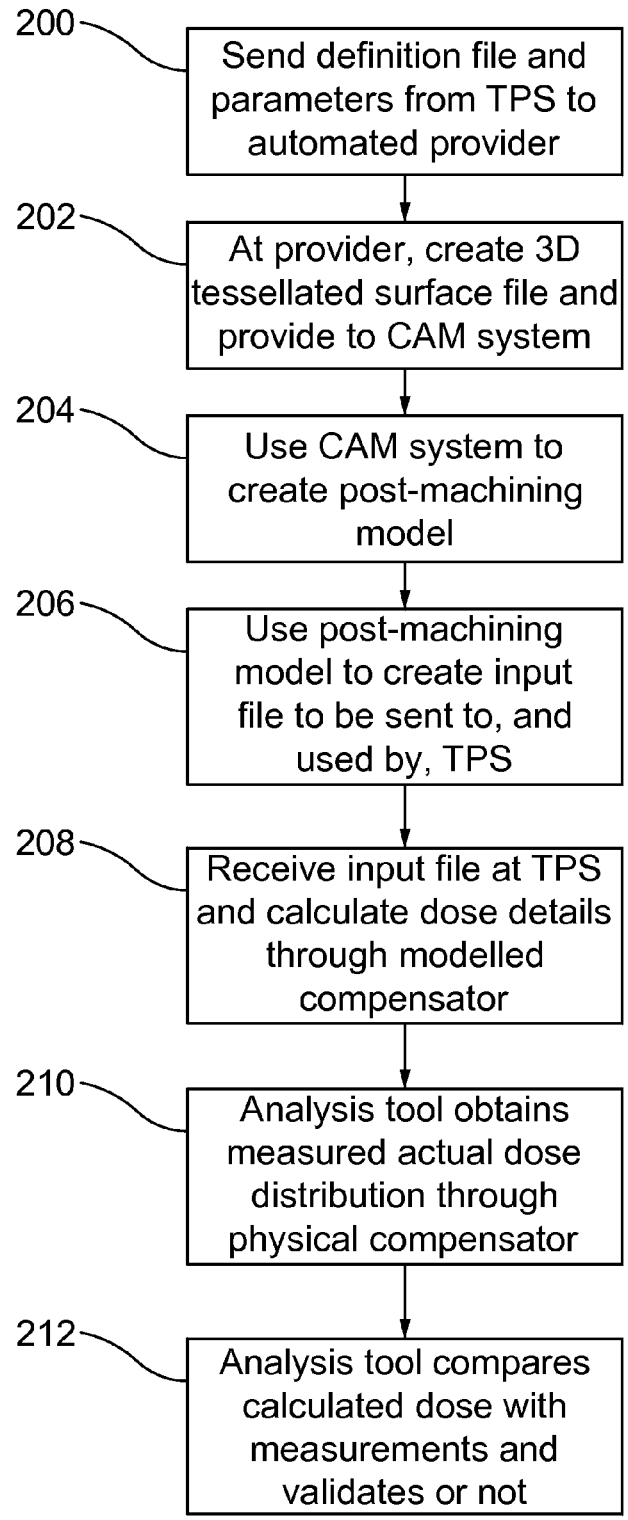
FIG. 2 is flow diagram that indicates the steps and systems involved in defining and validating the compensators.

Referring now to FIGS. 1 and 2, it is noted that, in accordance with the invention, a definition file is created by the TPS 104 to describe the radiation dose required for the tumor of a particular cancer patient. As indicated by step 200 of FIG. 2, this file can be sent from the TPS 104, or from one of the computers 102, via the Internet 130 (or other network) to the computer(s) 112. Typically also sent to the computer(s) 112 from the clinic 100 will be the size of the file and a number of parameters specific to the Linac 106. These parameters can include, for example, position and angle for treatment. Some of the data used to create the compensator typically will have been captured while performing certain performance measurements on the target Linac 106, and these parameters include the position of the compensator with respect to the radiation source, the linear attenuation coefficient for the specific treatment Linac 106 for the material from which the compensator is formed, the loading position of the compensator, the jaw identification for the Linac 106 internal beam limiting devices, and the mounting position on the accessory tray to align the compensator with the Linac 106 central axis.

The computer(s) 112 then can process the definition file and the parameters to create a file with a set of data that identifies a three-dimensional tessellated surface of a compensator that meets the requirements of the definition file and the parameters (step 202). (Tessellation is described in U.S. patent application Ser. No. 13/077,306 filed on Mar. 31, 2011, and the entirety of this U.S. patent application Ser. No. 13/077,306 is incorporated herein by reference.) This 3D compensator tessellated surface file is then provided to the CAM system (which is typically executed by the computer(s) 112, as indicated previously), and the CAM system uses the 3D surface file to create a post-machining computer model of the compensator (step 204). More particularly, it is noted that the file of the 3D tessellated surface is read by the CAM system, and the CAM system then calculates tool paths using a pre-defined set of milling cutters. The tool paths are contained and described within the contents of a tool path definition file created by the CAM system. These tool paths constitute all of the roughing, finishing, and profiling tool paths required to create a physical compensator on the machine 126. The CAM system has a function for replaying the tool path by simulating the cutter movements on a virtual block of material, and the resulting model thus replicates the actual tool movements and produces the material condition after machining, such as corner radii artifacts as a function of spherical cutters and areas that could not be cut because the tool could not physically reach the surfaces to be machined. It is this model that is the post-machining model that is created by the CAM system at step 204 of FIG. 2.

The tool path definition file created by the CAM system can be sent from the provider 110 or from the computer(s) 112 to the manufacturer 120. This file can be sent via the Internet 130, for example. One or more patient-specific compensators can then be physically created at the manufacturer 120 and then shipped to the clinic 100. Or the manufacturer 120 can create compensator molds and ship those molds to the clinic 100, as opposed to shipping the heavier finished compensator(s), and as disclosed in the incorporated-by-reference U.S. patent application Ser. No. 13/075,885 filed on Mar. 30, 2011.

The post-machining computer model created by the CAM system represents a 3D tessellated surface of the needed compensator and it can be data contained in a file, but, unlike the 3D compensator tessellated surface file that was initially provided to the CAM system, the CAM system-generated 3D tessellated surface file represents much more closely what will be the actual three-dimensional surface of the physical real-world compensator that will be created (either at the manufacturer 120 or at the clinic 100) and used with the Linac 106 to treat a cancer patient. This CAM system-generated 3D tessellated surface file is used by the computer(s) 112 to create an input file for sending to and use by the TPS 104 (step 206). This input file contains sufficient data formatted in a specific way particular to the receiving TPS 104 to enable the receiving TPS 104 to build within its internal database a geometric representation of sufficient accuracy to replicate the compensator assembly being placed in the path of the radiation beam. And this input file for importation into the TPS 104 typically does not have a standard format. It can be a series of points defining the actual surface in an x,y,z format, for example, or it can be an x,y position of beam entry into the compensator followed by a distance the beam travels through the attenuating material (i.e., the compensator) along the divergent beam path, as another example.

The input file can be sent from the provider 110 to the clinic 100, and the TPS 104 at the clinic 100 then uses this input file created by the computer(s) 112 to calculate dose distributions and generate a modified treatment plan for the patient. This is indicated as step 208 in FIG. 2. The modified treatment plan is created by the TPS 104 to capture and identify all of the necessary operating parameters of the Linac 106 to appropriately treat the patient with radiation given the contents of the CAM system-generated 3D tessellated surface file.

Actual radiation measurements are taken during a non-patient test of the Linac 106 with the physical finished patient-specific compensators in place. The measurements are obtained by using a radiation sensitive medium on the treatment couch of the Linac 106. The medium can be a film or an electronic dose measurement device such as a digital sensor array, for example.

The treatment plan created by the TPS 104 in step 208 is compared to the actual radiation measurements taken during the non-patient test to determine if there is a match (step 210). If the comparison is considered a match, then the physical finished patient-specific compensators used in the test are validated and approved for use in the Linac 106 to treat the cancer patient with radiation at the clinic 100 or else those compensators are not approved for use (step 212). The threshold for a match can be greater than 80% matching between the measurements and the plan determined by the TPS 104 in step 208, or the threshold can be greater than 85%, for example. Other possible thresholds are greater than 90% and greater than 95%. The comparison that is done to determine if there is a match or not can, in one embodiment, involve the following steps. First, the compensator description is imported into the TPS 104. A radiation physicist then applies the values such as jaw positions and amount of radiation for that field and other such data required by the TPS 104 in order for the TPS 104 to be able to properly calculate the dose delivered through the compensator at the given parameters. The physical compensator assembly is loaded into the target Linac 106 and the clinic's preferred radiation measuring system is placed onto the treatment couch of the Linac 106 to represent the patient. The treatment room is closed as per normal treatment conditions (that is, no personnel are present in the room). On the control console of the Linac 106, the treatment parameters pertaining to that specific field are entered, such as the amount of radiation in monitor units (MUs) and the jaw positions of the Linac 106. The Linac 106 is then switched on, and the radiation delivered in line with the console parameters to expose the chosen measurement medium on the couch. After exposure, the measurement medium is examined, and the results of the actual radiation delivery is compared to the calculated radiation delivery at step 208.

As indicated by steps 210 and 212, an analysis tool is used to obtain the measured actual dose distribution through the physical compensator and to do the comparison. The analysis tool can be software such as that available from Radiological Imaging Technology, Inc. of Colorado Springs, Colo. (www.radimage.com) when film is employed as the radiation measuring system or that available from Sun Nuclear Corporation of Melbourne, Fla. (www.sunnuclear.com) if a diode array is used as the radiation measuring system.

Certain embodiments according to the invention have been disclosed. These embodiments are illustrative of, and not limiting on, the invention. Other embodiments, as well as various modifications and combinations of the disclosed embodiments, are possible and within the scope of the disclosure.

What is claimed is:

1. A method of validating a compensator for use in a radiation therapy machine to treat a cancer patient, comprising:
    receiving a compensator description file including data representative of an actual surface of the compensator;
    determining, based on the compensator description file, a radiation treatment plan including operating parameters of the radiation therapy machine;
    comparing the determined radiation treatment plan to actual radiation measurements taken during a non-patient test of the radiation therapy machine with the compensator mounted to the machine; and
    when the comparing step results in a match according to a predetermined criteria, identifying the compensator as validated for use in the radiation therapy machine to treat the cancer patient.

2. The method of claim 1 wherein the step of determining the radiation treatment plan comprises modifying an original radiation treatment plan.

3. The method of claim 1 wherein the determining step comprises determining the intensity of the radiation beam produced by the radiation therapy machine.

4. The method of claim 1 wherein the compensator is identified as validated when the comparing step results in a match of 80% or greater.

5. The method of claim 1 wherein the compensator comprises a radiation attenuating material.

6. The method of claim 5 wherein the compensator is machined from a solid piece of material.

7. The method of claim 6 wherein the solid piece of material comprises tungsten, brass, or aluminum.

8. The method of claim 5 wherein the compensator is formed by compacting solid particulates into a mold.

9. The method of claim 8 wherein the solid particulates comprise crystalline tungsten powder.

10. The method of claim 1 wherein the validated compensator is used in intensity modulated radiation therapy (IMRT), proton radiation therapy, or cobalt radiation therapy.

* * * * *